United States Patent
Heid et al.

(10) Patent No.: US 10,838,030 B2
(45) Date of Patent: Nov. 17, 2020

(54) HYBRID EXAMINATION SYSTEM HAVING AN MR SCANNER, AN X RAY SOURCE AND AN X RAY DETECTOR

(71) Applicant: SIEMENS AKTIENGESELLSCHAFT, Munich (DE)

(72) Inventors: Oliver Heid, Erlangen (DE); Jürgen Heller, Spardorf (DE); Timothy Hughes, Wantage (GB); Michael Kleemann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 56 days.

(21) Appl. No.: 14/428,993

(22) PCT Filed: Sep. 21, 2012

(86) PCT No.: PCT/EP2012/068596
§ 371 (c)(1),
(2) Date: Mar. 18, 2015

(87) PCT Pub. No.: WO2014/044314
PCT Pub. Date: Mar. 27, 2014

(65) Prior Publication Data
US 2015/0247907 A1    Sep. 3, 2015

(51) Int. Cl.
*G01R 33/48* (2006.01)
*A61B 6/00* (2006.01)
(Continued)

(52) U.S. Cl.
CPC .......... *G01R 33/4812* (2013.01); *A61B 5/055* (2013.01); *A61B 6/035* (2013.01);
(Continued)

(58) Field of Classification Search
None
See application file for complete search history.

(56) References Cited

U.S. PATENT DOCUMENTS 6,241,671 B1 * 6/2001 Ritter ................ A61B 34/73
361/141
6,591,127 B1    7/2003 McKinnon
(Continued)

FOREIGN PATENT DOCUMENTS

CN    85109632 A    7/1986
CN    101347656 A    1/2009
(Continued)

OTHER PUBLICATIONS

English Translation for DE 102008045276.*
(Continued)

*Primary Examiner* — Oommen Jacob
*Assistant Examiner* — Shahdeep Mohammed
(74) *Attorney, Agent, or Firm* — Schmeiser, Olsen & Watts LLP

(57) ABSTRACT

An examination system including a magnetic resonance scanner having a solenoid for generating a magnetic field, the solenoid surrounding an examination chamber is provided. In addition, a first X-ray source and a first X-ray detector are provided in the examination chamber.

13 Claims, 4 Drawing Sheets

(51) Int. Cl.
  *A61B 6/03* (2006.01)
  *A61B 5/055* (2006.01)
  *G01R 33/34* (2006.01)
  *G01R 33/3815* (2006.01)
  *G01R 33/385* (2006.01)
  *A61B 6/04* (2006.01)

(52) U.S. Cl.
  CPC ............ *A61B 6/4417* (2013.01); *A61B 6/504* (2013.01); *A61B 6/5247* (2013.01); *G01R 33/34* (2013.01); *G01R 33/385* (2013.01); *G01R 33/3815* (2013.01); *A61B 6/0407* (2013.01); *F04C 2270/041* (2013.01); *G01R 33/34046* (2013.01)

(56) References Cited

U.S. PATENT DOCUMENTS

| | | | |
|---|---|---|---|
| 6,812,700 B2 * | 11/2004 | Fahrig | G01R 33/3875 324/307 |
| 2003/0123612 A1 | 7/2003 | Pelc | |
| 2004/0021464 A1 * | 2/2004 | Fahrig | G01R 33/3875 324/314 |
| 2004/0186377 A1 | 9/2004 | Sahatjian | |
| 2005/0096532 A1 | 5/2005 | Block et al. | |
| 2008/0171931 A1 | 7/2008 | Maschke | |
| 2008/0204012 A1 * | 8/2008 | Krueger | A61B 5/05 324/300 |
| 2009/0299170 A1 * | 12/2009 | Gebhardt | A61B 5/055 600/411 |
| 2010/0010337 A1 * | 1/2010 | Hagen | A61B 5/0555 600/411 |
| 2012/0150017 A1 * | 6/2012 | Yamaya | G01R 33/3806 600/411 |
| 2012/0310079 A1 * | 12/2012 | Henning | A61B 6/503 600/411 |

FOREIGN PATENT DOCUMENTS

| | | |
|---|---|---|
| CN | 101455574 A | 6/2009 |
| CN | 102519999 A | 6/2012 |
| CN | 103210318 A | 7/2013 |
| DE | 102008045276 A1 | 3/2010 |
| JP | H09502381 A | 3/1997 |
| JP | H10192268 A | 7/1998 |
| JP | 2005131408 A | 5/2005 |
| JP | 2008212667 A | 9/2008 |
| JP | 2009502257 A | 1/2009 |
| JP | 2011512999 A | 4/2011 |
| WO | WO 2012077064 A1 | 6/2012 |

OTHER PUBLICATIONS

Chinese Office Action dated Jun. 1, 2016; Application No. 201280075949.7; 18 pgs.
International Search Report—PCT/EP2012/068596—International Filing Date: Sep. 21, 2012; 2 pgs.
Chinese Office Action dated Feb. 4, 2017; Application No. 201280075949.7; 20 Pgs.
Fahrig, Rebecca et al. "A Truly Hybrid Interventional MR/X-Ray System: Feasibility Demonstration" Journal of Magnetic Resonance Imaging, vol. 13, pp. 294-300, 2001 // https://doi.org/10.1002/1522-2586(200102)13:2<294::AID-UMRI1042>3.0.CO;2-X; 7 pages.

* cited by examiner

HYBRID EXAMINATION SYSTEM HAVING AN MR SCANNER, AN X RAY SOURCE AND AN X RAY DETECTOR

CROSS-REFERENCE TO RELATED APPLICATIONS

This application claims priority to PCT Application No. PCT/EP2012/068596, having a filing date of Sep. 21, 2012, the entire contents of which are hereby incorporated by reference.

FIELD OF TECHNOLOGY

The following relates to an examination system and to a method for producing an angiogram.

BACKGROUND

Magnetic resonance tomographs for imaging diagnostics for medical purposes are known from the prior art. Magnetic resonance imaging uses the dependence of the relaxation times of excited nuclear spins on the environment of the atomic nuclei in order to obtain information relating to a spatial arrangement of different tissue types in a body of a patient. Magnetic resonance tomographs are suitable, in particular, for high contrast imaging of soft tissues.

X-ray units for imaging diagnostics for medical purposes are likewise known from the prior art. Radiography uses the different permeability of different tissue types for X-radiation to produce a view through a body part of a patient. It is possible in this case to produce moving images in real time.

US 2008/0171931 A1 describes a hybrid system comprising a magnetic resonance tomograph and an X-ray unit which makes it possible to record an image of a body part of a patient by means of the magnetic resonance tomograph, and subsequently to undertake an intervention on the body of the patient, optical control being performed by means of the X-ray unit.

SUMMARY

An aspect relates to an improved examination system. A further aspect relates to providing a method for producing an angiogram.

An examination system comprises a magnetic resonance tomograph with a cylindrical coil for generating a magnetic field. Here, the cylindrical coil surrounds an examination space. Arranged in said examination space are a first X-ray source and a first X-ray detector. Said examination system advantageously permits images to be obtained with high spatial resolution and good soft tissue contrast by using the methods of magnetic resonance imaging. Moreover, X-ray images with high temporal resolution can be prepared by means of the first X-ray source and the first X-ray detector. The integration of the magnetic resonance tomograph with the X-ray system formed from the X-ray source and X-ray detector ensures that anatomical information obtained by using the two methods is temporally and spatially consistent. The combination of the two imaging methods supplies sets of anatomical information which complement one another, thus increasing the amount of information that can be obtained overall. There is an advantageous improvement in the clinical effectiveness of the overall system as a result.

In one embodiment of the examination system, the first X-ray source and the first X-ray detector are rotatable about a rotation axis arranged in a longitudinal direction of the examination space. It is then advantageously possible to use the X-ray system formed from the X-ray source and X-ray detector to prepare X-ray images from different directions of view.

In one embodiment of the examination system, the first X-ray source and the first X-ray detector are rigidly interconnected. It is thereby advantageously ensured that, given a rotation of the X-ray source and X-ray detector about the rotation axis, the X-ray detector is arranged such that it can detect X radiation emitted by the X-ray source.

In one embodiment of the examination system, a gradient coil with a first gradient coil portion and a second gradient coil portion is arranged in the examination space. Here, the first gradient coil portion and the second gradient coil portion are spaced apart in an axial direction. Furthermore, the first X-ray source and the first X-ray detector are arranged between the first gradient coil portion and the second gradient coil portion. Given said arrangement, there is advantageously formed in the interspace between the first gradient coil portion and the second gradient coil portion a gradient field which permits a spatially resolved examination by means of magnetic resonance imaging. At the same time, the X-ray system formed from the X-ray source and X-ray detector is arranged in said interspace and thereby permits preparation of X-ray images of the same region, which is also displayed by means of magnetic resonance imaging. Optical obstruction or shading of the X radiation by the gradient coil is avoided by the arrangement of the X-ray system in the interspace between the gradient coil portions of the gradient coil.

In one embodiment of the examination system, a radiofrequency coil is arranged in the examination space. In one embodiment, said coil is arranged between the first gradient coil portion and the second gradient coil portion. The radiofrequency coil can advantageously serve to emit radiofrequency magnetic pulses and to receive signals emitted by relaxing nuclear spins. The arrangement of the radiofrequency coil in the interspace between the first gradient coil portion and the second gradient coil portion of the gradient coil makes it possible to examine by images the same part, arranged in the examination space, of a patient's body which is also detected by the X-ray system formed from the X-ray source and X-ray detector.

In one embodiment of the examination system, the radiofrequency coil is rigidly connected to the first X-ray source. The mutual orientation of the radiofrequency coil and X-ray source then advantageously remains constant even given a rotation of the X-ray system, formed from the X-ray source and X-ray detector, about the rotation axis. Influences on the X-ray system owing to the radiofrequency coil are thereby minimized. An absorption, effected by the radiofrequency coil, of X-radiation emitted by the X-ray source is temporally invariable. This advantageously enables artifacts effected by the radiofrequency coil to be minimized or removed in images prepared by the X-ray system.

In one embodiment of the examination system, a second X-ray source and a second X-ray detector are arranged in the examination space. Provision of two X-ray systems advantageously enables X-ray images to be recorded at a higher rate, renders it possible to reduce an X-ray dose and provides the possibility of simultaneously using X-rays of different energies. It is possible thereby to obtain additional information relating to perfusion behavior and a type and a composition of a tissue being examined.

In one embodiment of the examination system, the first X-ray source and the second X-ray source are rigidly interconnected. A viewing angle difference between the first X-ray source and the second X-ray source is then advantageously temporally constant.

In one embodiment of the examination system, the second X-ray source is offset from the first X-ray source by an angle with reference to a rotation about a rotation axis arranged in a longitudinal direction of the examination space. A body part of a patient which is to be examined can then advantageously be irradiated simultaneously from two directions by means of the two X-ray systems.

In one embodiment of the examination system, the angle is 90 degrees. It is then advantageously possible for the X-ray images generated by means of the two X-ray systems to be particularly easily correlated with one another.

An examination system of the above-named type is used in a method for producing an angiogram. The angiogram can then advantageously include information obtained by means of examination by magnetic resonance imaging and information obtained by means of an X-ray examination, as a result of which the angiogram produced by said method has a particularly high information content.

BRIEF DESCRIPTION

Some of the embodiments will be described in detail, with reference to the following figures, wherein like designations denote like members, wherein.

DETAILED DESCRIPTION

Figure 1:
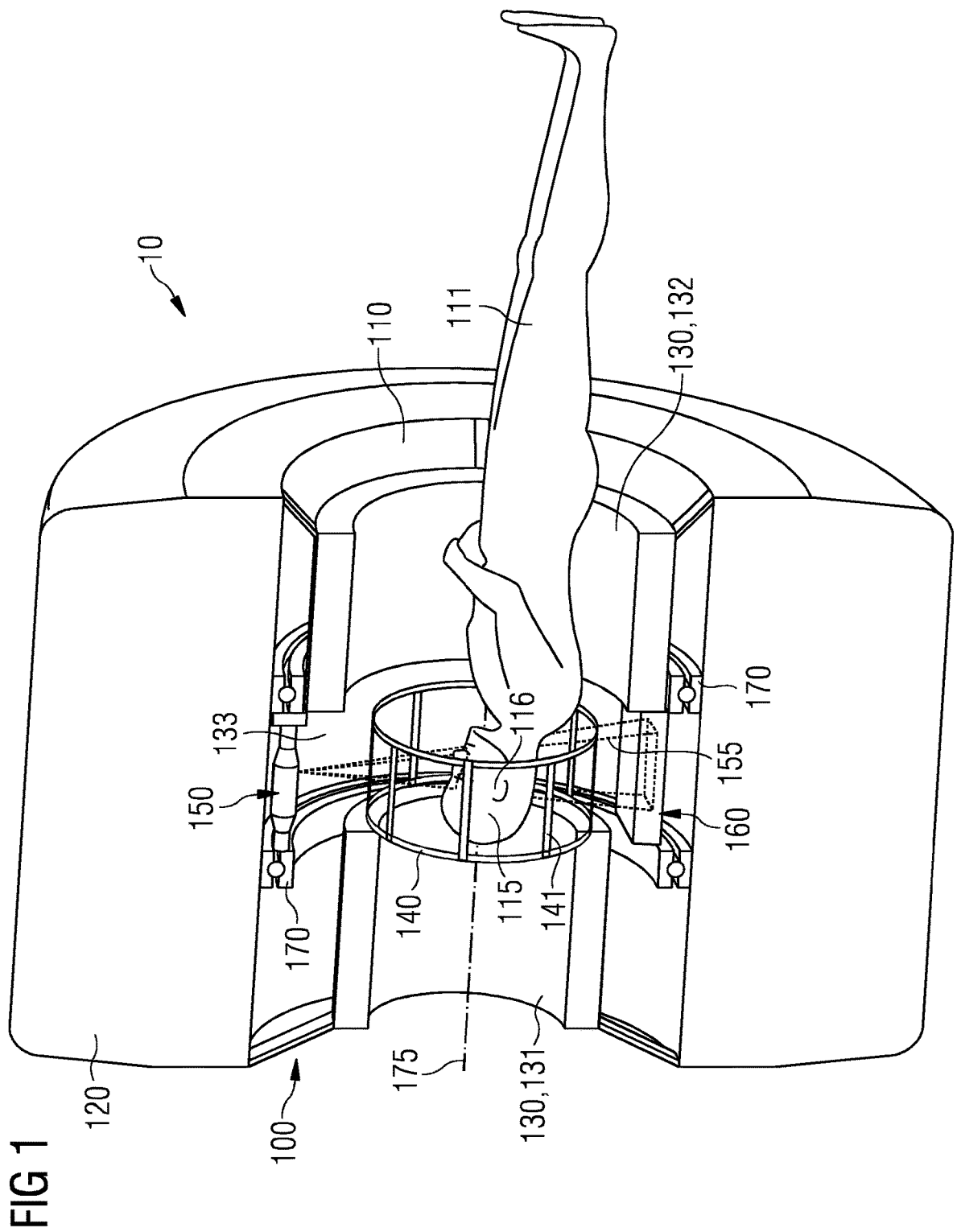
FIG. 1 shows a sectional perspective illustration of an examination system in accordance with a first embodiment.

FIG. 1 shows a schematically sectional perspective illustration of an examination system 10 in accordance with a first embodiment. The examination system 10 can serve the purpose of medical diagnostics. In particular, the examination system 10 can serve for treatment by angiography. The examination system 10 comprises a magnetic resonance tomograph 100. The magnetic resonance tomograph 100 has a cylindrical coil 120 which surrounds a tubular examination space 110. The cylindrical coil 120 is designed as an elongated hollow cylinder. The cylindrical examination space 110 serves for recording a schematically illustrated patient 111. In the example illustrated, a body part 116 (here, the head) of the patient 111 is arranged in a field of view 115 in the examination space 110 of the examination system 10 in order, with the aid of the examination system 10, to obtain images of the body part 116 of the patient 111 which are suitable for the purpose of medical diagnostics.

The cylindrical coil 120 of the magnetic resonance tomograph 100 serves to generate a strong static magnetic field in the examination space 110 by means of which a decay of energy between different alignments of the magnetic moments of the atomic nuclei of the body of the patient 111 is canceled out. By way of example, the cylindrical coil 120 can be designed as a superconducting magnet. The cylindrical coil 120 can, for example, be designed so as to generate a static magnetic field with a strength of between 0.2 tesla and 3 tesla or more. The magnetic field generated by the cylindrical coil 120 is preferably designed to be rather homogeneous, at least in the field of view 115 of the examination space 110. Under the influence of the static magnetic field generated by the cylindrical coil 120, the nuclear spins of the atomic nuclei of the body of the patient 111 precess about the axis prescribed by the magnetic field (Larmor precession).

In order to produce slice images of the body part 116, arranged in the field of view 115 of the examination space 110, of the patient 111, it is necessary to modify the homogeneous magnetic field generated by the cylindrical coil 120 as a function of position. The magnetic resonance tomograph 100 has a gradient coil 130 for this purpose. The gradient coil 130 is provided for the purpose of generating a magnetic gradient field for selective slice excitation and for spatial coding of a measurement signal during a measurement carried out by the magnetic resonance tomograph 100.

The gradient coil 130 comprises a first gradient coil portion 131 and a second gradient coil portion 132. The first gradient coil portion 131 and the second gradient coil portion 132 are each designed as a hollow cylinder and arranged coaxially with the cylindrical coil 120 in the examination space 110 surrounded by the cylindrical coil 120. In this case, the first gradient coil portion 131 and the second gradient coil portion 132 of the gradient coil 130 are spaced apart from one another in an axial direction so that an interspace 133 is formed between the first gradient coil portion 131 and the second gradient coil portion 132. The field of view 115 is located in the region of said interspace 132. In the example illustrated, the first gradient coil portion 131 has a smaller diameter than the second gradient coil portion 132. However, this is not absolutely necessary.

By irradiating an alternating magnetic field oriented perpendicular to the static magnetic field generated by the cylindrical coil 120 at a resonant frequency, it is possible, under conditions of phase synchronism, to deflect (excite) the nuclear spins, precessing about the axis of the static magnetic field, of the atoms of the body of the patient 111. The magnetic resonance tomograph 100 has a radiofrequency coil 140 for this purpose. The radiofrequency coil 140 is arranged in the interspace 133 between the first gradient coil portion 131 and the second gradient coil portion 132 of the gradient coil 130. The radiofrequency coil 140 surrounds two rings, arranged coaxially with the cylindrical coil 120, which are interconnected via a plurality of crossbars 141. The radiofrequency coil 140 is rotatable about a rotation axis 175 which corresponds to a longitudinal axis of the cylindrical coil 120 and of the examination space 110. The field of view 115 of the examination space 110 is arranged inside the radiofrequency coil 140. The radiofrequency coil 140 is suitable for irradiating radiofrequency magnetic pulses. Once an alternating magnetic field irradiated by the radiofrequency coil 140 has been switched off, the nuclear spins excited by the alternating magnetic field relax after a characteristic relaxation time and in doing so emit signals which are received by the radiofrequency coil 140. An image of the body part 116, arranged in the field of view 115, of the patient 111 can be reconstructed by mathematical methods from the signal data received by the radiofrequency coil 140.

The examination system 10 further comprises an X-ray system with an X-ray source 150 and an X-ray detector 160. The X-ray source 150 and the X-ray detector 160 are arranged in the interspace 133 between the first gradient coil portion 131 and the second gradient coil portion 132 of the gradient coil 130 in the examination space 110. The X-ray source 150 is designed to emit an X-ray beam 155 which passes through the field of view 115 and strikes the X-ray detector 160 after traversing the field of view 115. The X-ray system formed from the X-ray source 150 and X-ray detector 160 permits a rapid preparation of X-ray images of the body part 116, arranged in the field of view 115, of the patient 111 with a high temporal resolution.

The X-ray source 150 and the X-ray detector 160 are supported rotatably, by means of a bearing 170, about the rotation axis 175 and are rigidly interconnected. In this case, there is a phase difference of approximately 180 degrees between the X-ray source 150 and the X-ray detector 160 with reference to a rotation about the rotation axis 175. Arranging the X-ray system formed from the X-ray source 150 and X-ray detector 160 to be rotatable about the rotation axis 175 permits the body part 116, arranged in the field of view 115 of the examination space 110, of the patient 111 to be irradiated from different directions of view, and thus permits views to be prepared through the body part 116 from different directions of view. The common arrangement of the radiofrequency coil 140 of the magnetic resonance tomograph 100 and of the X-ray system, formed from the X-ray source 150 and X-ray detector 160, in the interspace 133 about the field of view 115 ensures that the anatomical information obtained by using the methods of magnetic resonance imaging with the magnetic resonance tomograph 100 and by using the methods of X-ray examination by the X-ray system is temporally and spatially consistent. The sets of information obtained by using the two modes of examination complement one another in this case.

Figure 2:
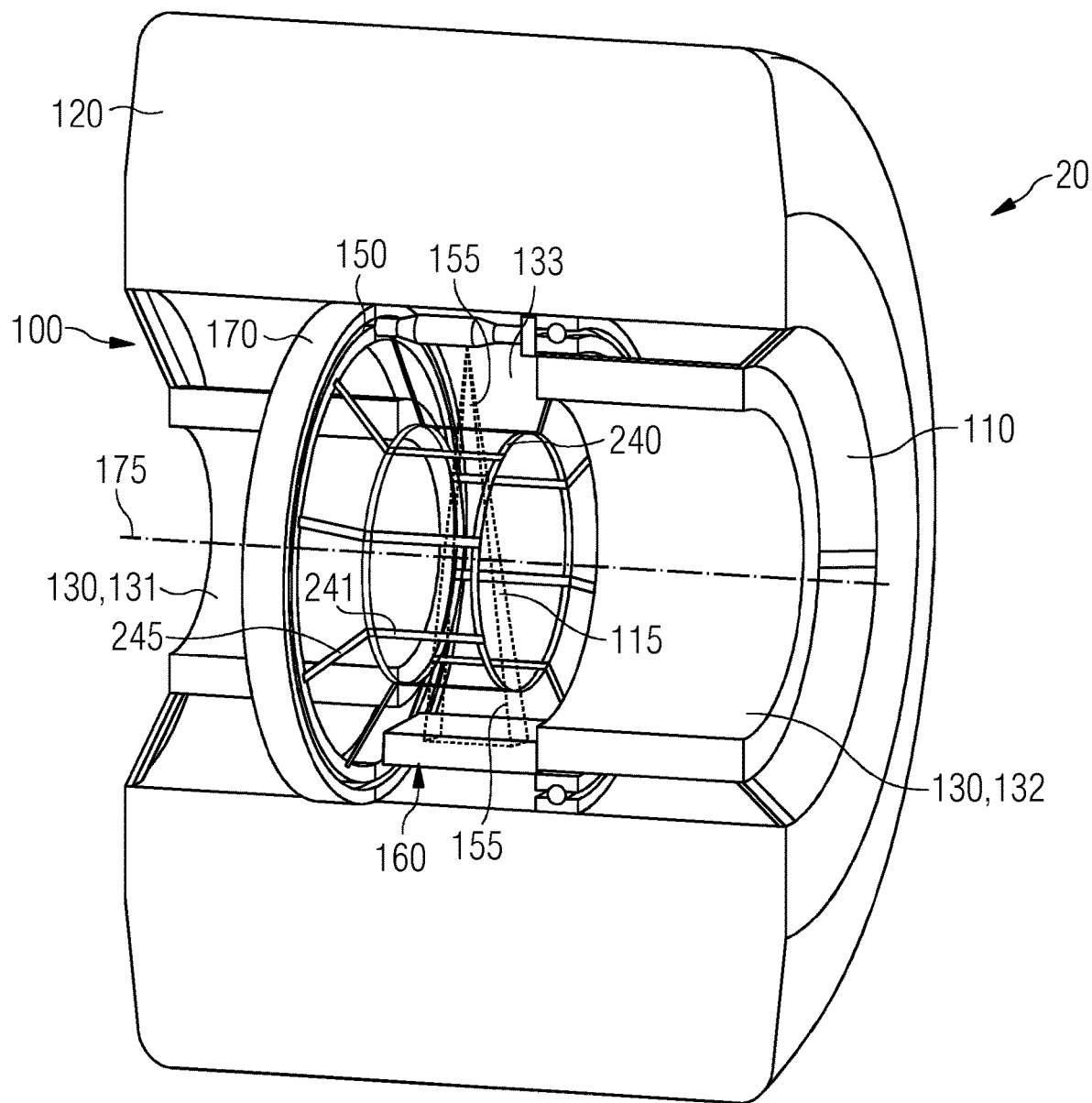
FIG. 2 shows a sectional perspective illustration of an examination system in accordance with a second embodiment.

FIG. 2 shows a schematic perspective sectional illustration of an examination system 20 in accordance with a second embodiment. The examination system 20 exhibits marked similarities with the examination system 10 of FIG. 1. For this reason, corresponding components are provided with the same reference symbols and are not described anew below.

In the examination system 20, instead of the radiofrequency coil 140 a radiofrequency coil 240 is provided, and is arranged in the examination space 110 around the field of view 115 in the interspace 133 between the first gradient coil portion 131 and the gradient coil portion 132 of the gradient coil 130. The radiofrequency coil 240, in turn, has two rings which are arranged coaxially with the cylindrical coil 120 and are interconnected by means of a plurality of crossbars.

However, in contrast to the radiofrequency coil 140, the radiofrequency coil 240 is rigidly connected by means of a rigid connection 245 to the X-ray system formed by the X-ray source 150 and X-ray detector 160. The radiofrequency coil 240 is therefore supported rotatably about the rotation axis 175 in common with the X-ray system by means of the bearing 170. The radiofrequency coil 240 is thereby rotatable about the rotation axis 175 under conditions of phase synchronism in relation to the X-ray system formed from the X-ray source 150 and X-ray detector 160. During a rotation of the radio-frequency coil 240 and of the X-ray system about the rotation axis 175, the relative arrangement between the radiofrequency coil 240, the X-ray source 150 and the X-ray detector 160 remains constant.

This offers the advantage that influences caused by the radiofrequency coil 240 and exerted on X-ray images recorded by means of the X-ray system are temporally constant and can be minimized. Since the X-ray source 150, the X-ray detector 160 and the radiofrequency coil 240 are rigidly interconnected, an absorption, caused by the radiofrequency coil 240, of the X-ray beam 155 is temporally invariant. This enables any possible artifacts in X-ray images prepared by means of the X-ray system, for example artifacts effected by the crossbars 241 of the radiofrequency coil 240, to be minimized or to be removed. For example, the radiofrequency coil 240, the X-ray source 150 and the X-ray detector 160 can be mutually oriented so that the X-ray beam 155 does not strike one of the crossbars 241 of the radiofrequency coil 240. It is likewise possible for artifacts occurring unchanged over time to be eliminated by computation by using the methods of digital image processing.

Figure 3:
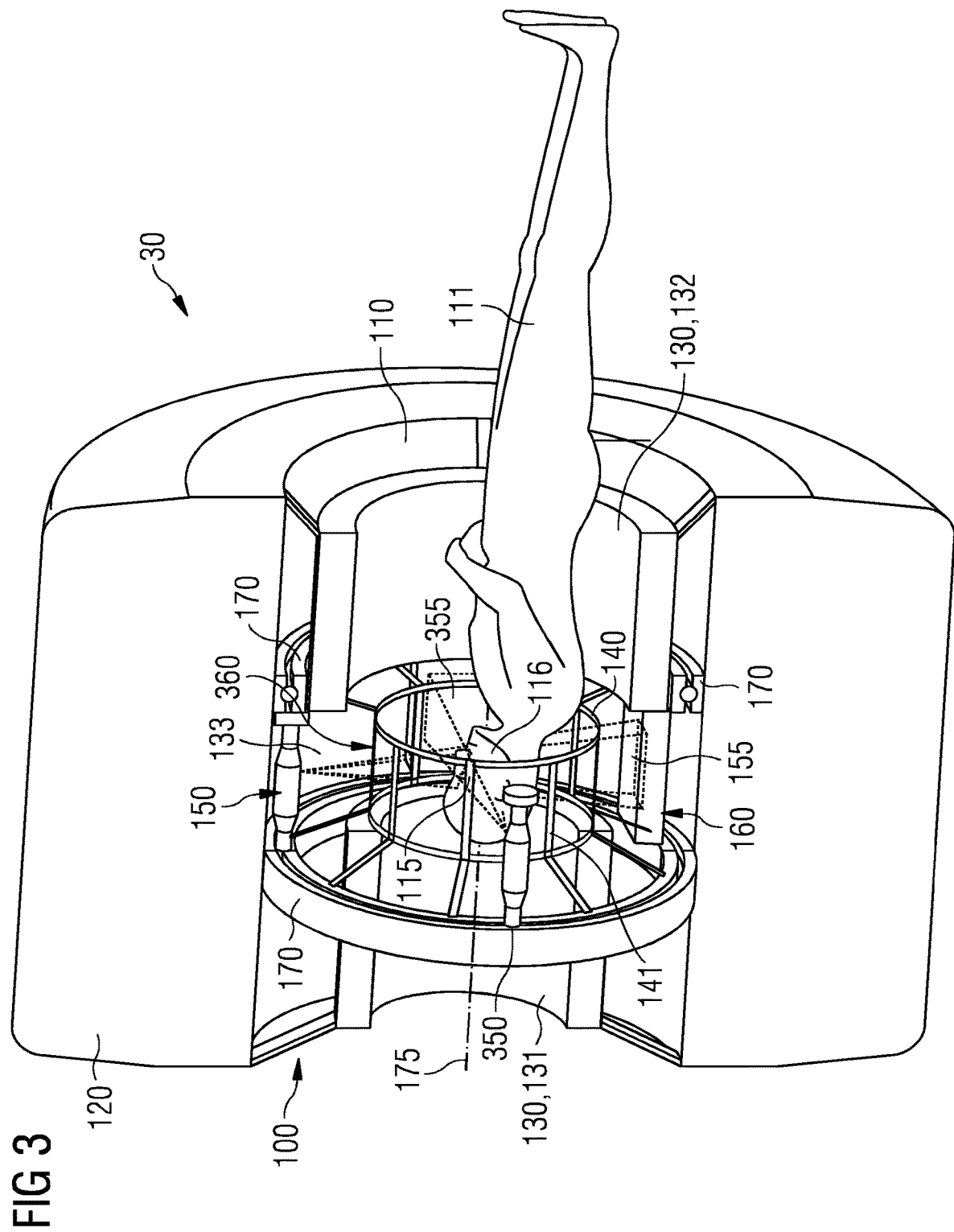
FIG. 3 shows a sectional perspective illustration of an examination system in accordance with a third embodiment.
Figure 4:
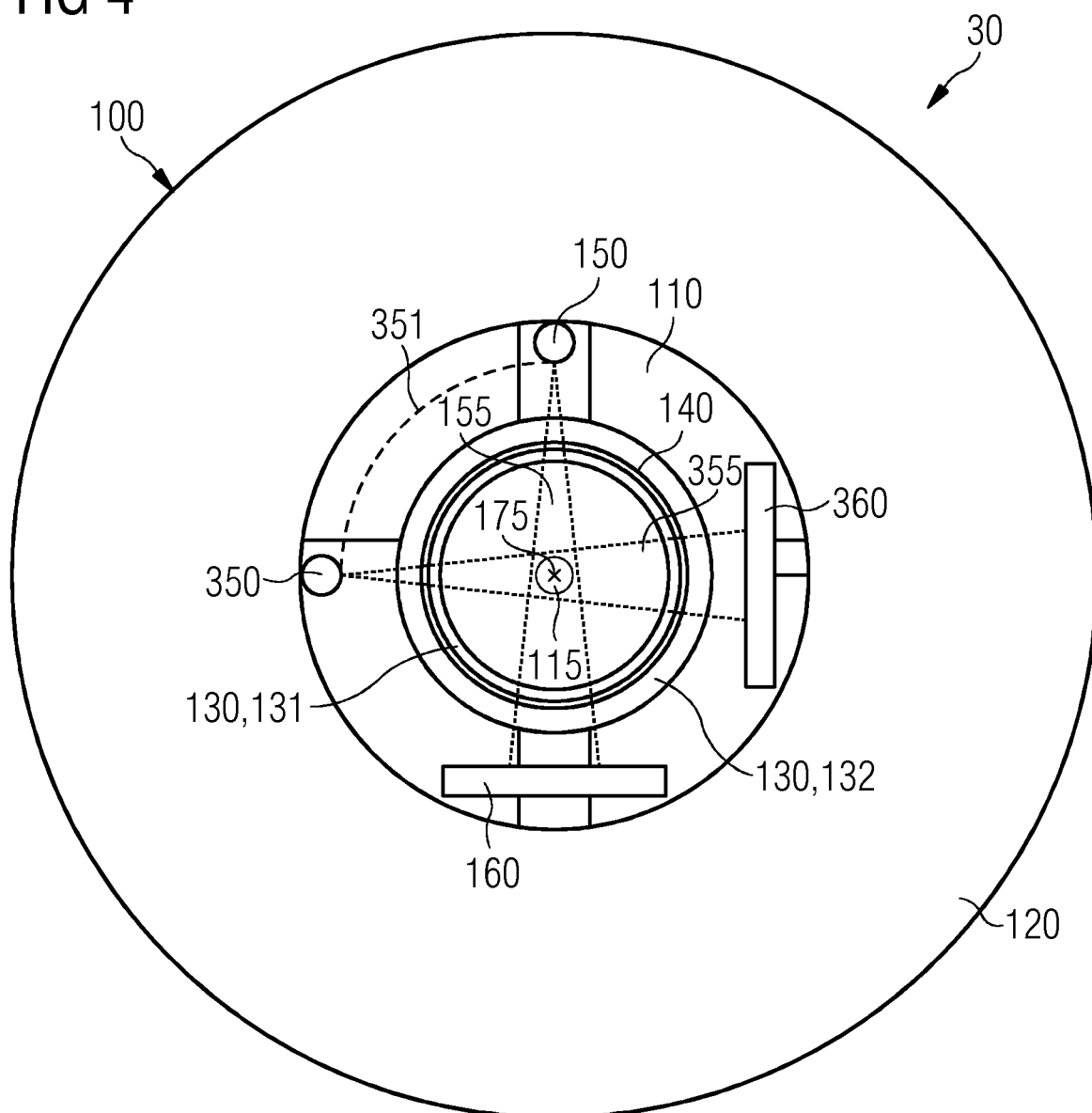
FIG. 4 shows a further sectional illustration of the examination system in accordance with the third embodiment.

FIG. 3 shows a schematic perspective sectional illustration of an examination system 30 in accordance with a third embodiment. FIG. 4 shows a further sectional illustration of the examination system 30. The section runs vertically to the rotation axis 175 in the illustration of FIG. 4. The examination system 30 has similarities with the examination system 10 of FIG. 1. Mutually corresponding components are therefore provided with the same reference symbols and are not described anew in more detail below.

In addition to the components of the examination system 10, a second X-ray source 350 and a second X-ray detector 360 are present in the examination system 30. The second X-ray source 350 and the second X-ray detector 360 form a second X-ray system. The second X-ray source 350 and the second X-ray detector 360 are likewise arranged in the interspace 133 between the first gradient coil portion 131 and the second gradient coil portion 132 of the gradient coil 130 and are oriented so that a second X-ray beam 355 emitted by the second X-ray source 350 passes through the field of view 115 before it strikes the second X-ray detector 360.

The second X-ray source 350 and the second X-ray detector 360 are likewise supported rotatably about the rotation axis 375 by means of the bearing 170. The second X-ray source 350 and the second X-ray detector 360 are rigidly interconnected in such a way that a constant angular relationship of preferably approximately 180 degrees exists between the second X-ray source 350 and the second X-ray detector 360 with reference to a rotation about the rotation axis 175.

In a preferred embodiment, the X-ray source 150 and the second X-ray source 350 are also rigidly interconnected in such a way that a constant angle 351 always exists between the X-ray source 150 and the second X-ray source 350 with reference to a rotation about the rotation axis 175. The angle 351 can be between 0 degrees and 180 degrees. In a preferred design, the angle 351 is approximately 90 degrees. X-ray images recorded by means of the X-ray system formed from the X-ray source 150 and the X-ray detector 160, and X-ray images recorded by means of the second X-ray system formed by the second X-ray source 350 and the second X-ray detector 360 then show the body part 116, arranged in the field of view 115, of the patient 111 from mutually perpendicular directions of view.

The presence of two X-ray systems in the examination system 30 offers the advantage that it is possible to record X-ray images at an even higher rate and image repetition frequency. Moreover, this opens up the possibility of reducing an X-ray dose. The two X-ray systems can also be operated at different wavelengths or energy levels. It is thereby possible to obtain additional information relating to the body part 116, arranged in the field of view 115, of the patient 111. For example, it is possible thereby to obtain additional information relating to the perfusion behavior or to tissue types of the body part 116.

In the examination systems 10, 20, 30, the magnetic resonance tomograph 100 and the X-ray systems are preferably operated simultaneously in each case. However, it is also possible to operate only either the magnetic resonance tomograph or the X-ray system for individual examinations. The two modes of examination can also be performed sequentially in time.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. An examination system comprising:
a magnetic resonance tomograph having a cylindrical coil for generating a magnetic field, the cylindrical coil surrounding an examination space;
a first X-ray source and a first X-ray detector arranged in the examination space and surrounded by the cylindrical coil; and
a radiofrequency coil arranged in the examination space, wherein a field of view shared by the magnetic resonance tomograph and the first X-ray source in the examination space is arranged inside the radiofrequency coil, the radiofrequency coil having two rings that are arranged coaxially with the radiofrequency coil and are interconnected by a plurality of crossbars;
wherein the radiofrequency coil is rigidly connected to the first X-ray source within the examination space, by means of a rigid connection, such that the radiofrequency coil and the first X-ray source are rotatable together with respect to the cylindrical coil of the magnetic resonance tomograph within the examination space;
wherein the rigid connection defines a mutual structural orientation between the first X-ray source and the radiofrequency that enables artifacts in X-ray images caused by the crossbars of the radiofrequency coil to be avoided as a result of X-ray beams not striking the crossbars of the radiofrequency coil due to the mutual structural orientation.

2. The examination system as claimed in claim 1, wherein the first X-ray source and the first X-ray detector are rotatable about the rotation axis arranged in a longitudinal direction of the examination space.

3. The examination system as claimed in claim 1, wherein the first X-ray source and the first X-ray detector are rigidly interconnected.

4. The examination system as claimed in claim 1, wherein the radiofrequency coil is rotatable about the rotation axis arranged in a longitudinal direction of the examination space.

5. The examination system as claimed in claim 1, wherein a gradient coil with a first gradient coil portion and a second gradient coil portion is arranged in the examination space, the first gradient coil portion and the second gradient coil portion being spaced apart in an axial direction, the first X-ray source and the first X-ray detector being arranged between the first gradient coil portion and the second gradient coil portion.

6. The examination system as claimed in claim 5, wherein the radiofrequency coil is arranged between the first gradient coil portion and the second gradient coil portion.

7. The examination system as claimed in claim 1, wherein a second X-ray source and a second X-ray detector are arranged in the examination space.

8. The examination system as claimed in claim 7, wherein the first X-ray source and the second X-ray source are rigidly interconnected.

9. The examination system as claimed in claim 8, wherein the second X-ray source is offset from the first X-ray source by an angle with reference to a rotation about a rotation axis arranged in a longitudinal direction of the examination space.

10. The examination system as claimed in claim 9, wherein the angle is 90 degrees.

11. A method of producing an angiogram by utilizing the examination system of claim 1, comprising:
operating the magnetic resonance tomograph to obtain a first set of information based on magnetic resonance imaging;
operating the first X-ray source to obtain a second set of information based on X-ray imaging; and
producing the angiogram from the first set of information and the second set of information.

12. An examination system comprising:
a magnetic resonance tomograph having a cylindrical coil for generating a magnetic field, the cylindrical coil surrounding an examination space; and
a first X-ray source and a first X-ray detector arranged in the examination space and surrounded by the magnetic cylindrical coil, the first X-ray source and the first X-ray detector being rotatable about a rotation axis arranged in a longitudinal direction of the examination space, by means of a bearing disposed within the examination space;
wherein a radiofrequency coil positioned within the examination space is rigidly connected to the first X-ray source within the examination space, by means of a rigid connection, such that the radiofrequency coil and the first X-ray source are rotatable together with respect to the cylindrical coil of the magnetic resonance tomograph within the examination space, the radiofrequency coil having two rings that are arranged coaxially with the radiofrequency coil and are interconnected by a plurality of crossbars;
wherein the rigid connection defines a mutual structural orientation between the first X-ray source and the radiofrequency that enables artifacts in X-ray images caused by crossbars of the radiofrequency coil to be avoided as a result of X-ray beams not striking the crossbars of the radiofrequency coil due to the mutual structural orientation.

13. The examination system as claimed in claim 12, wherein the bearing is positioned against the cylindrical coil.

* * * * *